(12) United States Patent
Walton et al.

(10) Patent No.: US 9,261,403 B2
(45) Date of Patent: Feb. 16, 2016

(54) INLINE SPECTROSCOPIC READER AND METHODS

(75) Inventors: Ian D. Walton, Redwood City, CA (US); William E. Doering, Santa Clara, CA (US); Michael J. Natan, Los Altos, CA (US)

(73) Assignee: SICPA HOLDING SA (CH)

( * ) Notice: Subject to any disclaimer, the term of this patent is extended or adjusted under 35 U.S.C. 154(b) by 7 days.

(21) Appl. No.: 13/819,397

(22) PCT Filed: Aug. 31, 2011

(86) PCT No.: PCT/US2011/050008
§ 371 (c)(1),
(2), (4) Date: Feb. 27, 2013

(87) PCT Pub. No.: WO2012/030988
PCT Pub. Date: Mar. 8, 2012

(65) Prior Publication Data
US 2013/0155402 A1    Jun. 20, 2013

Related U.S. Application Data

(60) Provisional application No. 61/378,552, filed on Aug. 31, 2010.

(51) Int. Cl.
*G01J 3/44* (2006.01)
*G01J 3/28* (2006.01)
(Continued)

(52) U.S. Cl.
CPC ............. *G01J 3/28* (2013.01); *G01J 3/0208* (2013.01); *G01J 3/0218* (2013.01); *G01J 3/0272* (2013.01);
(Continued)

(58) Field of Classification Search
USPC .......................................................... 356/301
See application file for complete search history.

(56) References Cited

U.S. PATENT DOCUMENTS 5,717,209 A   2/1998   Bigman et al.
6,313,423 B1  11/2001  Sommer
(Continued)

FOREIGN PATENT DOCUMENTS

| EP | 1030740 | 10/2001 |
|---|---|---|
| JP | 2007-082607 | 4/2007 |
| WO | WO 2007/011389 | 1/2007 |

OTHER PUBLICATIONS

International Search Report and the Written Opinion of the International Searching Authorityfor International Application No. PCT/US2011/050008 mailed Feb. 1, 2012.
(Continued)

*Primary Examiner* — Kara E Geisel
*Assistant Examiner* — Omar Nixon
(74) *Attorney, Agent, or Firm* — Swanson & Bratschun, L.L.C

(57) ABSTRACT

An inline spectroscopic reader having a light source, one or more optics heads, a spectrometer and a data processing system in digital communication with the spectrometer detector. The optics heads include transmission optics providing for the illumination of a target with light from the light source and detection optics providing for the collection of light from the target. Typically, the target is moving with respect to the optics head during spectroscopic interrogation. The spectroscopic reader is thus an inline reader well suited to provide spectrum based production or analytical decision making in real time as the target moves along a production or analysis line. Also disclosed are methods including the steps of illuminating a target with light from a light source; collecting light from the target; obtaining a digitized spectrum with a spectrometer; extracting information content from the digitized spectrum; and basing a contemporaneous process decision upon the information content.

14 Claims, 11 Drawing Sheets

(51) Int. Cl.
*G01J 3/02* (2006.01)
*G01N 21/85* (2006.01)
*G01N 21/89* (2006.01)
*G07D 7/12* (2006.01)

(52) U.S. Cl.
CPC ............ *G01J 3/0291* (2013.01); *G01J 3/0294* (2013.01); *G01J 3/2803* (2013.01); *G01J 3/44* (2013.01); *G01N 21/85* (2013.01); *G01N 21/8901* (2013.01); *G07D 7/122* (2013.01)

(56) References Cited

U.S. PATENT DOCUMENTS

| | | |
|---|---|---|
| 6,486,948 B1 | 11/2002 | Zeng |
| 6,514,767 B1 | 2/2003 | Natan |
| 6,707,548 B2 | 3/2004 | Kreimer et al. |
| 6,861,263 B2 | 3/2005 | Natan |
| 7,116,414 B2 | 10/2006 | Long |
| 7,443,489 B2 | 10/2008 | Natan |
| 7,656,525 B2 | 2/2010 | Zhao et al. |
| 2002/0039186 A1* | 4/2002 | Rosenberg .................. 356/432 |
| 2003/0020912 A1* | 1/2003 | Norton et al. ................ 356/369 |
| 2005/0019784 A1* | 1/2005 | Su et al. ......................... 435/6 |
| 2006/0121602 A1* | 6/2006 | Hoshizaki et al. ......... 435/288.7 |
| 2007/0165210 A1 | 7/2007 | Wang |

OTHER PUBLICATIONS

Patent Examination Report dated Feb. 19, 2015 for corresponding Australian Application No. 2011295974.
Japanese Office Action dated Oct. 27, 2015 for Japanese Patent Application No. P2013-527274.

* cited by examiner

INLINE SPECTROSCOPIC READER AND METHODS

CROSS REFERENCE TO RELATED APPLICATIONS

This application is a §371 national phase application of and claims priority to PCT/US2011/050008, filed on Oct. 31, 2011, which claims priority to U.S. Provisional Patent Applications No. 61/378,552, filed on Aug. 31, 2010, both of which are incorporated in their entirety by reference herein.

BACKGROUND

Certain materials exhibit intrinsic optical properties that can be detected and analyzed spectroscopically. Other materials or items which are not inherently spectroscopically active can be marked with a spectroscopically active marker or tag. The detection and analysis of spectroscopically active materials or tags is common in laboratory settings where a sample of material may be spectroscopically interrogated and analyzed. In this case, the intrinsically spectroscopically active substance or the taggants must be measured with a detector. In some cases the detector is the human eye (e.g. strong upconverters or strongly fluorescent species). In other cases detection is accomplished with a device or instrument (the detector). In such an instance, the detector may use software to aid in data acquisition, processing, or analysis.

One common characteristic of many known detectors is a tendency to operate slowly, with long interrogation times, for example 0.1-10 seconds and long data analysis times, for example 0.1-10 seconds. This is true whether the objects being interrogated harbor a taggant, or whether an intrinsic optical property of the object is being measured. Thus, such detectors and readers are not well-suited for inline applications, where a large number of items are analyzed in real time, and where the total time allotted for each analysis and possibly process control decision is small, for example less than 1 second.

Where such in line instrumentation does exist, the information content provided is very simple. The embodiments disclosed herein are direct toward overcoming one or more of the limitations noted above.

SUMMARY OF THE EMBODIMENTS

One embodiment is an inline spectroscopic reader having a light source, one or more optics heads, a spectrometer and a data processing system in digital communication with the spectrometer detector. The optics heads include transmission optics providing for the illumination of a target with light from the light source and detection optics providing for the collection of light from the target. The transmission and detection optics may be physically housed together or physically separated from each other. In embodiments where the transmission and detection optics pairs are physically separated each functional pair comprises one optics head.

In many embodiments, the target is moving with respect to the optics head, transmission optics and detection optics. Therefore, the spectroscopic reader may be implemented as an inline spectroscopic reader because the apparatus is well suited to provide spectroscopic analysis, and spectrum based production or analytical decision making in real time as the target moves along a production or analysis line.

The light source may be implemented with any source producing illumination suitable for use in spectroscopic analysis. For example, the light source may be a monochromatic source or may radiate light energy at selected discreet wavelengths. In other implementations the light source could be a polychromatic light source. Typical light sources include various types of lasers or light emitting diode (LED) sources.

The spectrometer element may be implemented with any type of spectrometer including but not limited to a Raman spectrometer. The data processing system may be implemented with any type of data processor or computer providing for substantially contemporaneous spectroscopic analysis of the light collected from the target.

The inline spectroscopic reader may include one, two or any number of optics heads. The optics heads in multiple optics head embodiments may be oriented to view different sides, surfaces or faces of a target object.

In multiple optics head embodiments, the optics heads may be in optical communication with one or multiple light sources and spectrometers. Fiber optic coupling may be used between a lesser number of light sources, a lesser number of spectrometers and a greater number of optics heads for example.

The illumination provided at the target by the light source may be a spot or area illumination having selected dimensions or a linear illumination zone having selected dimensions.

The target can be a substance, material or item which is inherently spectroscopically active or which has a component or constituent which is spectroscopically active. Alternatively, the target can be a substance material or item which has been marked or tagged with a spectroscopically active marker or tag. The marker or tag can be a solid or liquid.

The data processing system is configured to extract and act upon information content derived from a digitized spectrum provided by the detector of the spectrometer. In many embodiments, the information content is complex information contents. Complex information content is defined herein as information content having more than the minimum required complexity necessary to support a given processing or analytical decision. For example, a single spectrum may be analyzed to determine whether or not multiple emission peaks are present. The presence or absence of multiple emission peaks may be relied upon to determine a binary processing decision, for example, whether or not to reject an item. Thus, the data processing system in selected embodiments provides for the autonomous implementation of a processing or analytical decision based upon complex information content.

An alternative embodiment is a method of inline spectroscopy including the steps of illuminating a target with light from a light source; collecting light from the target; obtaining a digitized spectrum with a spectrometer from the collected light; extracting information content from the digitized spectrum; and basing a contemporaneous process decision upon the information content extracted from the digitized spectrum.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 1:
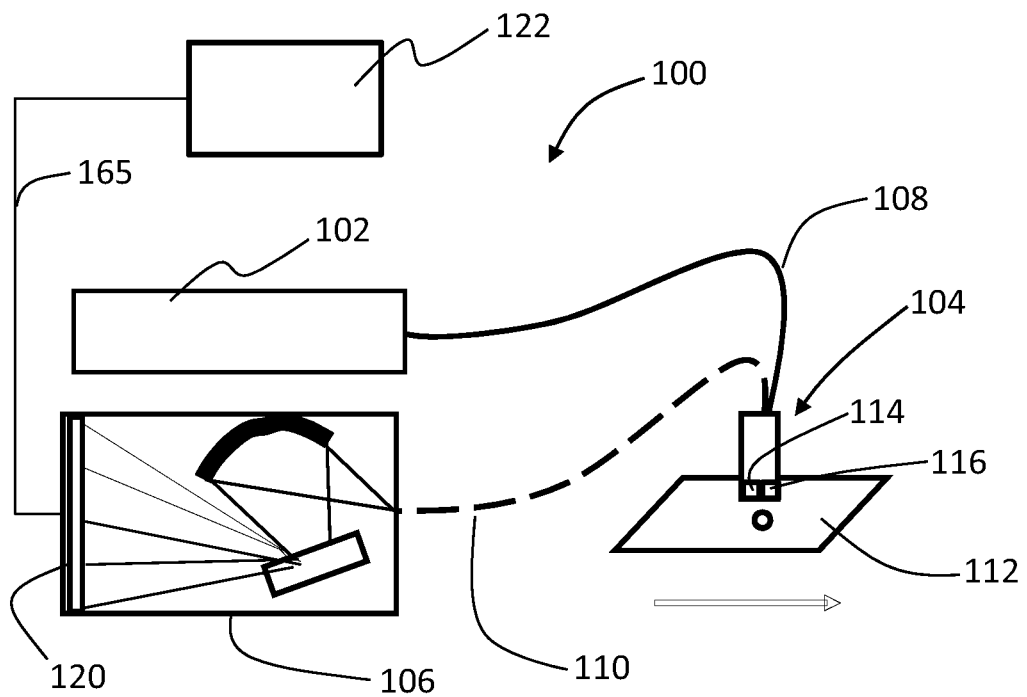
FIG. 1 is a schematic diagram of an inline reader embodiment as disclosed herein.

A schematic representation of one embodiment of an inline reader 100 as disclosed herein appears in FIG. 1. The inline reader 100 includes an illumination source 102, an optics head 104 and a spectrometer 106. In the illustrated system the optics head 104 is connected in optical communication with the illumination source 102 and spectrometer 106 via fiber optics 108 and 110. Alternatively, the illumination source 102, optics head 104 and spectrometer 106 could be connected in optical communication with each other using any combination of optical elements suitable for the transmission of light including but not limited to lenses, prisms, mirrors, free air optical transmission or the like. The illumination source 102, optics head 104 and spectrometer 106 could be positioned separately as illustrated in FIG. 1. Alternatively, the illumination source 102, optic head 104 and spectrometer 106 could be located within a single housing of any suitable size.

The light source 102 can be implemented with a light source producing illumination suitable for use in spectroscopic analysis. The light source may be a monochromatic source, alternatively the light source may radiate light energy at selected discrete wavelengths and alternatively the light source could be a polychromatic light source. For example, the light source 102 may be implemented with a laser, a vertical cavity surface emitting laser (VCSEL) or light emitting diode (LED), although other types of suitable light sources are possible.

Excitation light from the light source 102 is directed at a target 112 with the optic head 104. In addition, an optical emission from the target 112 is received at the optic head and transmitted to the spectrometer 106 using fiber optics or other optical transmission elements as described above. Thus the optics head includes transmission optics 114 providing for the illumination of the target 112 with light from the light source 102 and detection optics 116 providing for the collection of light from the target and transmission of light to the spectrometer 106 for analysis. The transmission and detection optics may be physically housed together or separated from each other. In embodiments where the transmission optics 114 and detection optics 116 pairs are physically separated, each functional pair still comprises one optics head 104.

As described in detail below, the target can be either a substance, material or item or the target can be a spectroscopically active tag associated with a substance, material or item. In all cases the target 112 is moving with respect to the transmission optics, typically as part of a manufacturing, sorting, verification, authentication, quality assurance or other automated or semi-automated process. For example, the target 112 could be moving on a conveyor belt past the optical head 104 or the target could be an object such as mail or a tag placed upon mail that is interrogated by the in line reader as it is being sorted by a conventional sorting machine. In other embodiments, the target could be a fluid flowing in a fluid channel past the optical head. Any type of industrial or laboratory process that involves a moving substance, material or item could be enhanced with the disclosed embodiments of inline readers. Accordingly, "inline" is defined herein as the substantially contemporaneous spectroscopic interrogation of a target 112, while the target moves with respect to the inline reader 112.

Possible targets 112 may be generally grouped into two broad categories. The first broad category includes substances, materials or items which are inherently spectroscopically active or which have a component or constituent which is spectroscopically active. Such a substance, material or item is described herein as possessing an intrinsic signal. The second broad category of target 112 includes substances, materials or items which have been marked or tagged with a spectroscopically active marker or tag. The marker or tag can be a solid or a liquid. Many alternative types of markers or tags are disclosed below. The scope of the embodiments disclosed herein is not limited to any particular inherently spectroscopically active material described in detail or any particular tag or marker. The disclosed inline reader embodiments and methods can be implemented with any type of inherently spectroscopically active material or marker or tag.

Figure 2:
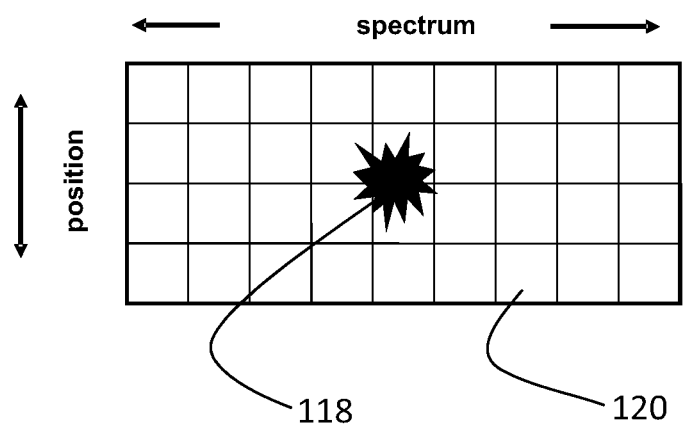
FIG. 2 is a schematic diagram of the detector of the inline reader embodiment of FIG. 1.

FIG. 2 is a schematic representation of an illumination spot 118 produced on the spectroscopic detector 120 by the optic head 104 of the FIG. 1 embodiment. The illuminated spot of FIG. 2 is approximately 100 to 150 microns in diameter, but could be enlarged or focused to an arbitrary size from 1 micron to 5 centimeters. Alternatively, line illumination is possible, where the line diameter is from 1 micron to 1 inch, and the line length is from 2 microns to 10 inches. The signal emitted from the target 112 is collected by the detection optics 116 of the optic head 104 and relayed to the spectrometer 106 via optical fiber 110. The fiber 110 is imaged onto the detector 120 of the spectrometer 106 to form the spot 118. As noted above alternative methods of conveying the signal emitted from the target to the detector 120 of the spectrometer 106 are within the scope of this disclosure. The detector 120 is typically a CCD array detector, for example, an array of 2048 pixels in width and 64 pixels in height. Other types of detector are possible. The spectrometer 106 disperses the spectrum of the collected light across a width of the detector 120. The detector 120 is read out to a data processing system 122 and bins of the spectrum are created. The binned or digitized spectrum is analyzed by the data processing system 122 as described in detail below to extract information content.

Typically, an inline reader 100 as described herein will be implemented to monitor or interrogate a series of targets 112 that pass the optical head 104 at a speed associated with the applicable manufacturing, sorting, quality assurance, verification, authentication or other process. Target movement and inline contemporaneous analysis raises substantial challenges that must be overcome to provide effective and flexible operability. In an industrial scale processing implementation, multiple targets can enter the illumination zone of the inline reader 100 in a variety of orientations. For example, oblong pharmaceutical tablets present in a process monitoring line might be aligned such that the long axis is parallel to the direction of motion, or they might be aligned such the that long axis is perpendicular to the direction of motion, or any of the orientations in between. Likewise, there may not be a single preferred orientation, and all the tablets are randomly oriented with respect to the direction of motion. Likewise, the tablets may have different lateral positions on a conveyor belt, such that a line drawn between two adjacent tablets is not parallel to the edges of the belt. In this instance, a small, fixed illumination spot might not interrogate certain tablets that are not aligned with the majority. Another representative example would be a mail sorting machine. Each envelope has different dimensions, therefore it would not be possible to interrogate or detect all stamps (or all zip codes) with a single, small, fixed interrogation beam.

Inline processing featuring high throughput spectroscopic interrogation must therefore accommodate the variations in the position and orientation of the targets being interrogated, and the type of item as well. For example, an inline reader associated with a sorting instrument might have to identify 2 to 20 different kinds of items. Packaging for express mail typically is available in 2 to 4 different sizes, to accommodate different sizes of paper and different thicknesses of paper stacks, and there may be a need to separate such items by size. Even if there is a single item, multiple orientations are available. Pharmaceutical tablets typically have text on a single side. If the ink used for text contains a taggant, and assuming the text says "ASPIRIN", four orientations are possible: text face up-N side first, text face up-A side first, text face down-N side first, text face down-A side first. Moreover, the text may not even be symmetric with respect to the tablet dimensions, i.e. it could be closer to one edge than another.

Therefore, the reader must be able to detect an inherently active region or a tagged feature over a variety of spatial locations. In order to save cost only one spectrometer 106 and one light source 102 could be used with multiple optics heads 104. Thus, a single spectrometer could be used to interrogate multiple regions of the target 112.

Figure 3:
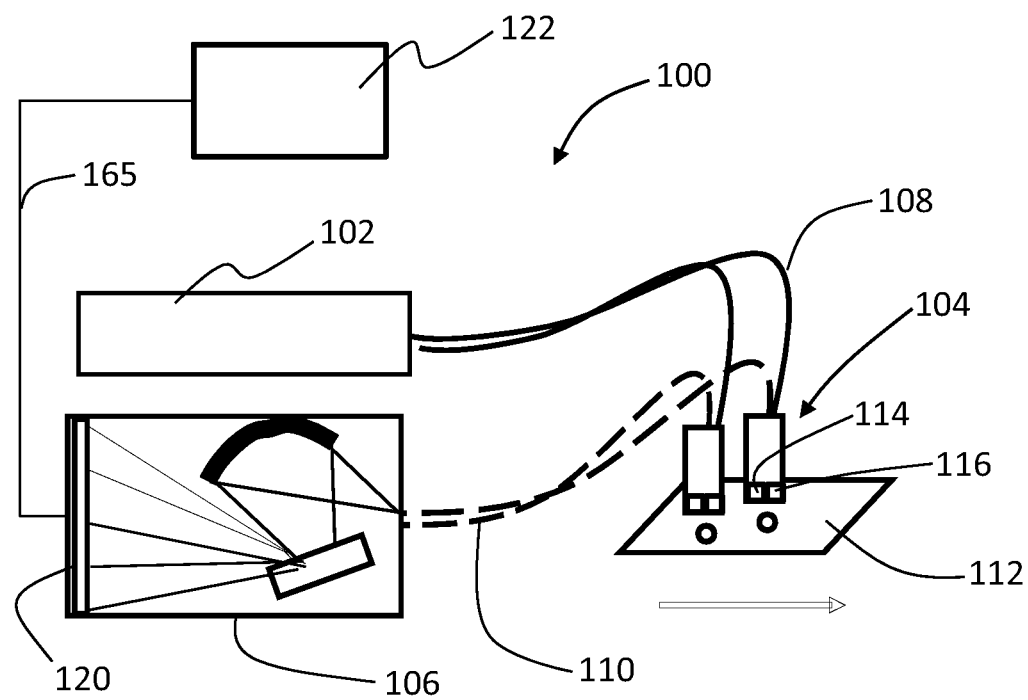
FIG. 3 is a schematic diagram of an alternative inline reader embodiment.
Figure 4:
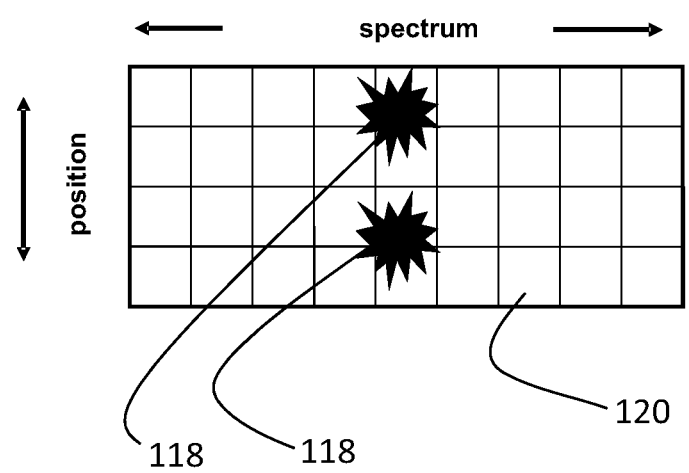
FIG. 4 is a schematic diagram of the detector of the inline reader embodiment of FIG. 3.

As shown in FIGS. 3 and 4, a fiber optically coupled detector 100 allows for this architecture since multiple optic heads 104 can be coupled to a single spectrometer 106 and/or light source 102 by combining the ends of the fibers into one assembly or bundle. Conversely, each fiber optic head 104 may use its own light source 102 to enable higher power or multiple excitation wavelengths or wavelength ranges.

Figure 5:
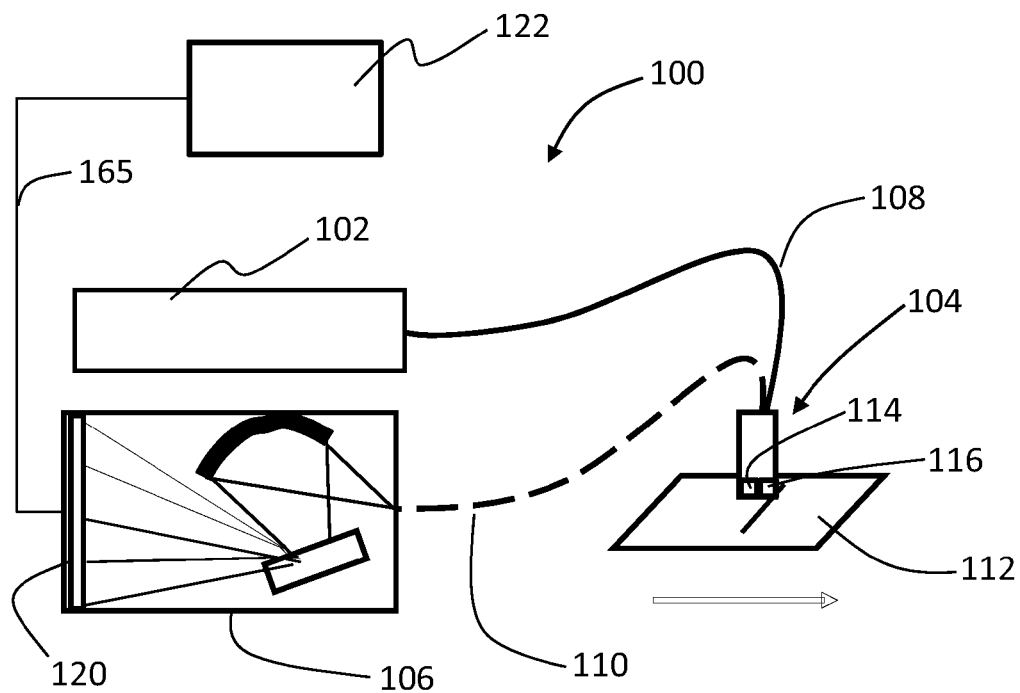
FIG. 5 is a schematic diagram of an alternative inline reader embodiment.
Figure 6:
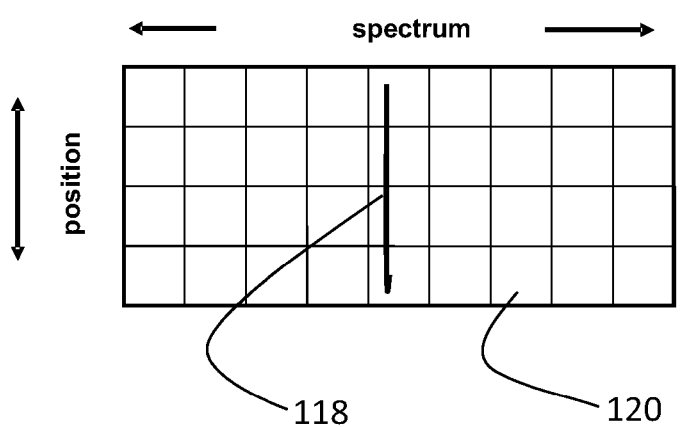
FIG. 6 is a schematic diagram of the detector of the inline reader embodiment of FIG. 5.

A larger portion of one side of the tagged item or an item with an intrinsic signal can be interrogated by either using multiple optics heads, as shown in FIG. 3 or 4 or one optic head 104 that illuminates the target and collects light along a linear illumination zone 124, as shown in FIGS. 5 and 6. When two or more optics heads 104 are used, then the light transmitted through each head can be imaged onto the detector 120 at distinct positions on the detector 120. Each row of discrete spectrum can be read out and digitized separately and thus the location of the tagged feature or intrinsic signal can be determined. Alternatively, all positions can be read out at one time or summed. Thus the final spectrum could contain a sum of the taggant or intrinsic signal and all other signals. In such an embodiment, spatial information is lost, but the presence of the taggant or intrinsic signal is confirmed. The summing process can also be performed optically, for example by using a fiber bundle system or fused fiber system where each collection fiber from the optical head is combined into a single spot that is imaged onto the detector. The same detector read out scheme to maintain spatial information can be employed when line illumination or collection is used. Alternatively, all position signals can be summed during readout to create one single spectrum. Alternatively, the collected signal from the line can be reformed into a single fiber spot that is transmitted to the detector.

Figure 7:
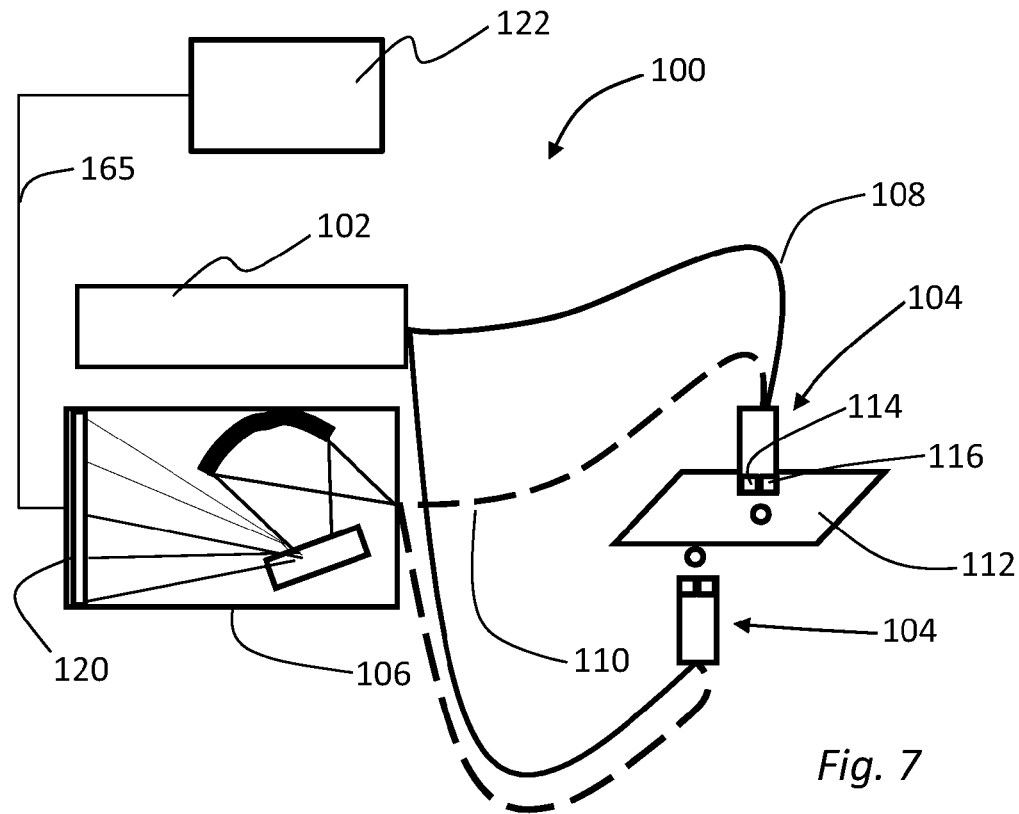
FIG. 7 is a schematic diagram of an alternative inline reader embodiment.
Figure 8:
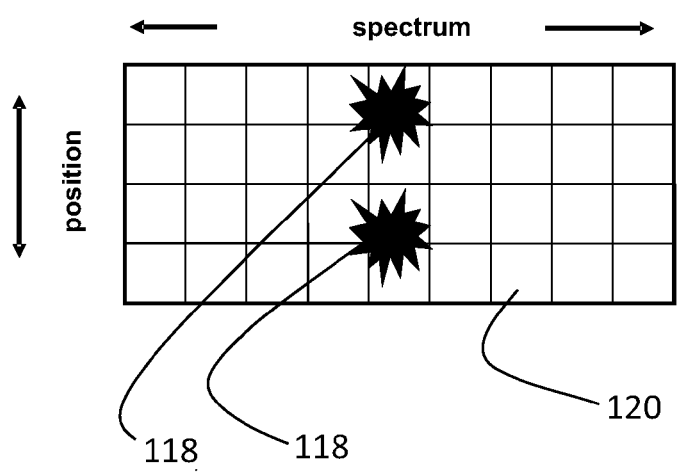
FIG. 8 is a schematic diagram of the detector of the inline reader embodiment of FIG. 7.

Alternatively, multiple sides of a target 112 can be simultaneously interrogated using multiple optics heads 104, as shown in FIGS. 7 and 8. When two or more optics heads 104 are used, the light collected by each head can be imaged onto the detector 120 at distinct positions. As illustrated, a single light source 120 may be used for both optics heads 104, or each may have its own light source. As noted above, each spectrum can be read out and digitized separately and thus the orientation of the tagged feature or intrinsic signal can be determined. Alternatively, all positions can be read out at one time or summed such that spatial information is lost, but the presence of the taggant or intrinsic signal is confirmed. The summing process can also be performed optically but using a fiber bundle system or fused fiber system where each collection fiber from the optical head is combined into a single spot that is imaged onto the detector.

Figure 9:
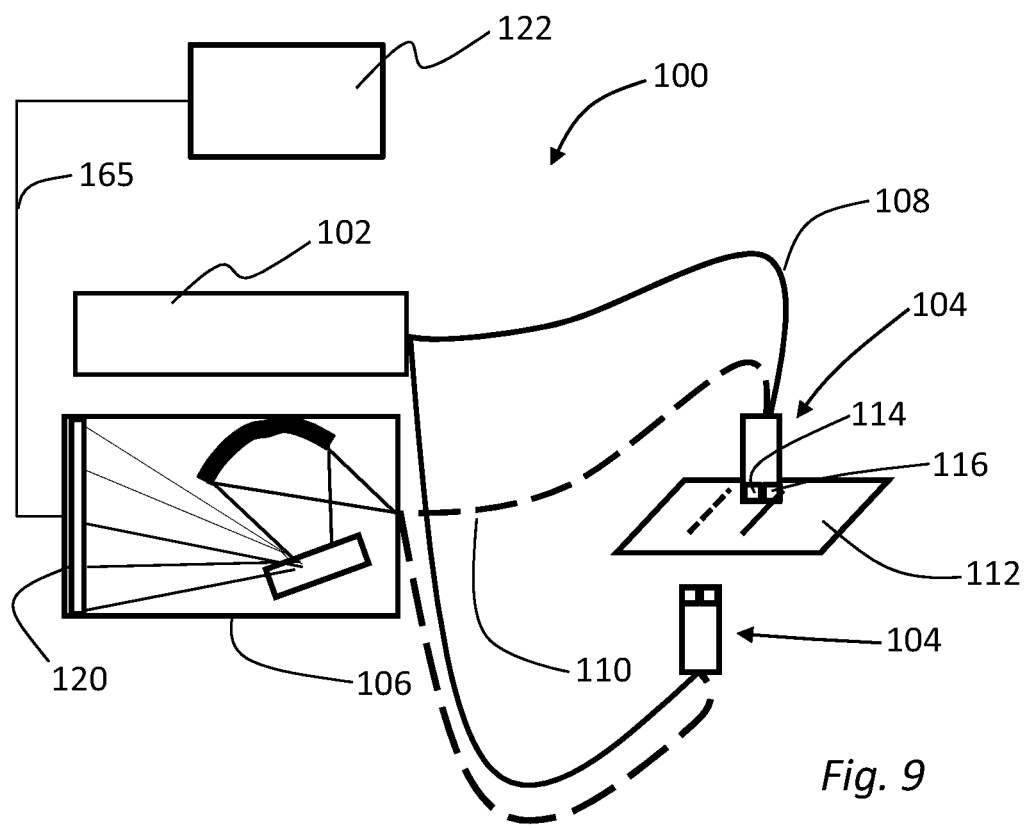
FIG. 9 is a schematic diagram of an alternative inline reader embodiment.
Figure 10:
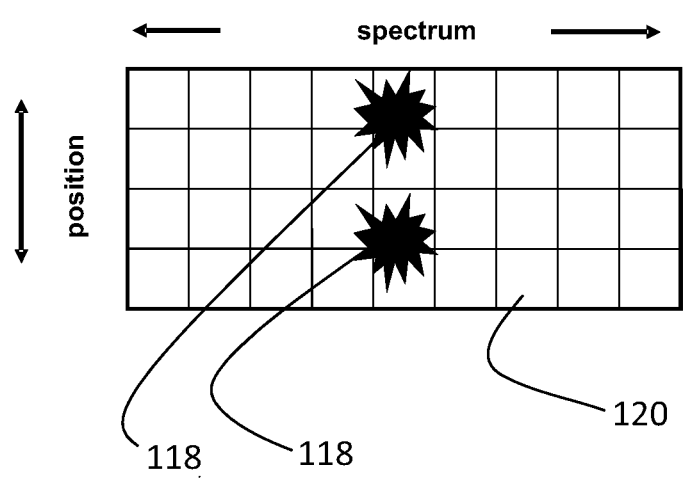
FIG. 10 is a schematic diagram of the detector of the inline reader embodiment of FIG. 9.

Line illumination can be employed with multiple optics heads 104, as illustrated in FIGS. 9 and 10. As is true with a single line of illumination 124, spatial information can be maintained by reading each appropriate position spectrum separately. Alternatively, all positions can be summed when reading out the CCD detector.

Figure 11:
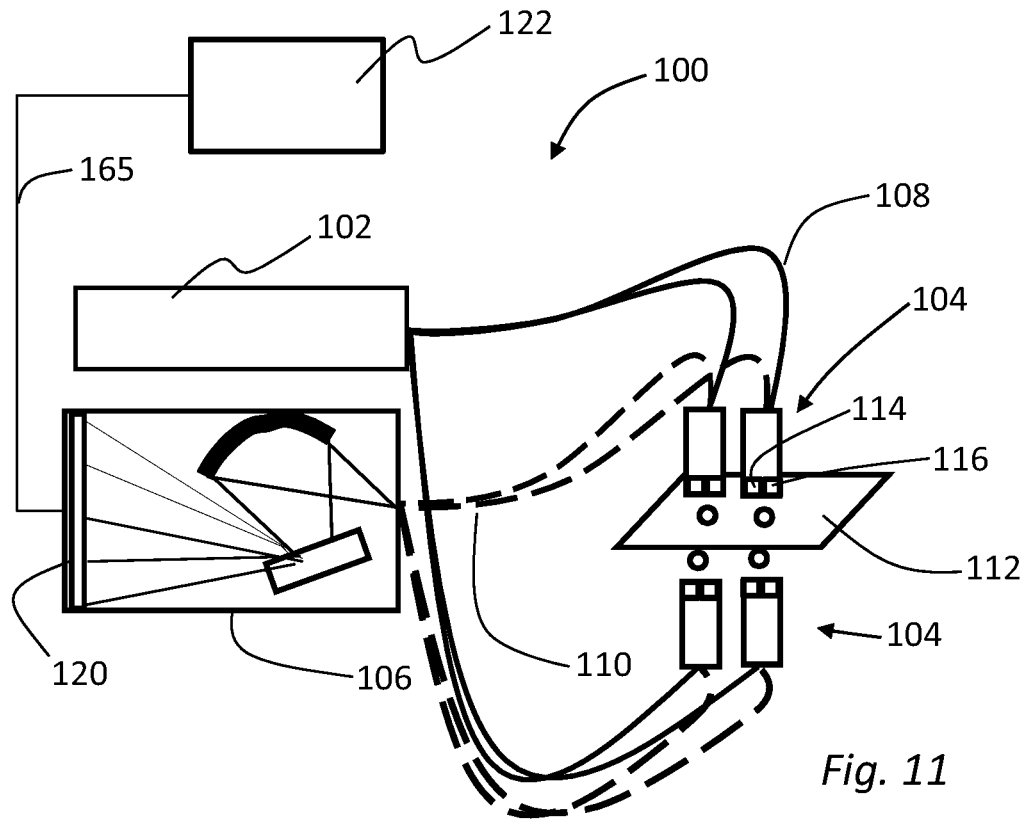
FIG. 11 is a schematic diagram of an alternative inline reader embodiment.
Figure 12:
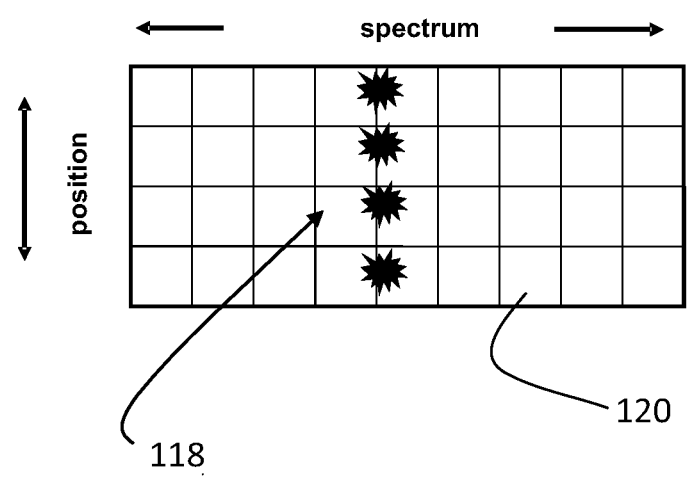
FIG. 12 is a schematic diagram of the detector of the inline reader embodiment of FIG. 11.

An alternative configuration is illustrated in FIGS. 11 and 12. In this configuration multiple optic heads 104 are used to detect signals from multiple sides (shown as the top and bottom) of the passing target 112. As in all previous configurations, the spectrum from each individual optic head 104 can be imaged separately on the detector and read out distinctly. Alternatively, all positions can be summed during readout. Alternatively, all positions can be summed optically by grouping all collection fibers into one bundle or a single fused fiber. The bundle or single fused fiber is then optically coupled to the spectrometer.

In certain situations, targets to be interrogated using an inline reader exhibit 3-dimensional (3-D) anisotropy. Such targets can have significantly different profiles of materials that lead to varying intrinsic signals or different profiles of taggants applied in a given spot or location. For example, a tagged document or plastic wrapping may have ink on both sides, but a taggant may be only incorporated onto a single side. Alternatively, certain pharmaceutical tablets contain two substances, one on the top half and another on the bottom half.

It would be advantageous to be able to read the document or the pill independent of which side is pointed up toward the optical head 104. As described above, this problem may be solved by incorporating multiple optical heads 104 into the reader 100. Alternatively, the target may exhibit sufficient transparency to allow interrogation light to reach the signal-generating material from any side. There are multiple ways to achieve a functional degree of transparency. (1) The target may be made sufficiently thin that the attenuated light transmitted through the target still is sufficiently intense to return a suitable signal. This can be accomplished for normal thickness paper, or single sheets of plastic packaging. (2) A light source can be selected that provides a wavelength where extinction by the target is minimized. Typically, longer wavelengths lead to less absorption. (3) A substantially transparent material may be the target, an example of this being clear liquids or clear plastics.

Figure 13:
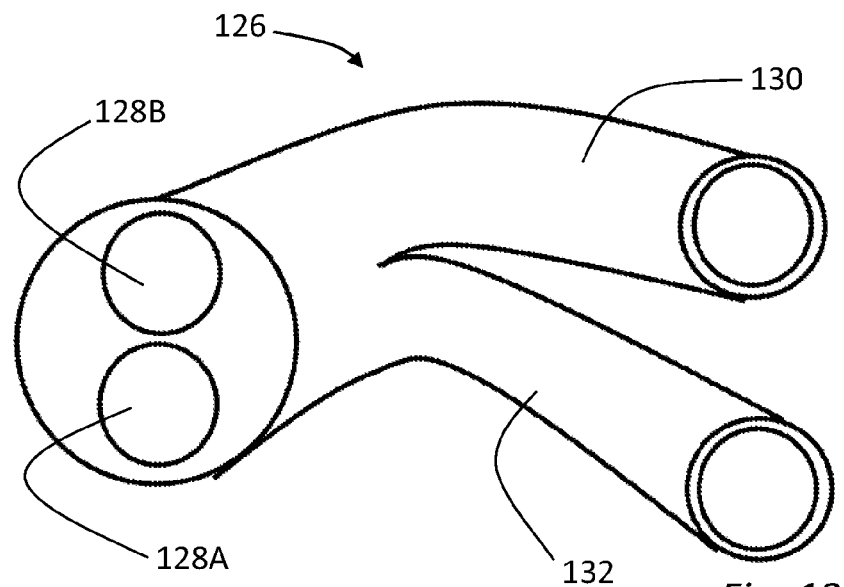
FIG. 13 is a schematic diagram of an optical fiber assembly as disclosed herein.

An example of a useful fiber optic assembly 126 for inline reader systems 100 having multiple optical heads 104 is illustrated in FIG. 13. The fiber optics assembly 126 consists of two multimode optical cores 128A and 128B of select diameter, for example, 100 microns. The two fiber cores are assembled into a single end termination or connector (not shown in FIG. 13). Both cores 128A and 128B may be covered in the same sheath for a portion of the length of the fiber assembly. At one point the two fiber cores can be separated into individual fibers 130 and 132 with their own sheaths and terminating into their own individual connectors. Each connector will then be connected to a separate optics head 104. A similar assembly design can also be used to provide illumination to multiple optics heads from a fewer number of light sources 102.

The inline reader 100 may be used to obtain one or more spectra from a target. In addition, the obtained spectrum or spectra will be analyzed to extract information content as described in detail below. The extracted information content may be relied upon to make one or more autonomous processing decisions. For example the information content derived from the spectrum may be used to make autonomous, contemporaneous processing decisions including but not limited to whether an item should be accepted or rejected, whether an item is high quality or low quality, whether an item is authentic or non-authentic, whether an item is in the correct location and/or at the correct time in a supply chain, and so forth. The foregoing processing decisions may be based upon simple information content or complex information content. As used herein, the term "simple information content" is defined as information content having the minimum degree of complexity required to support a given processing decision. The term "complex information content" is information content having more than the minimum required complexity necessary to support a given processing decision. Examples of decisions based upon both simple and complex information content are described with respect to FIGS. 14 and 15.

Figure 15:
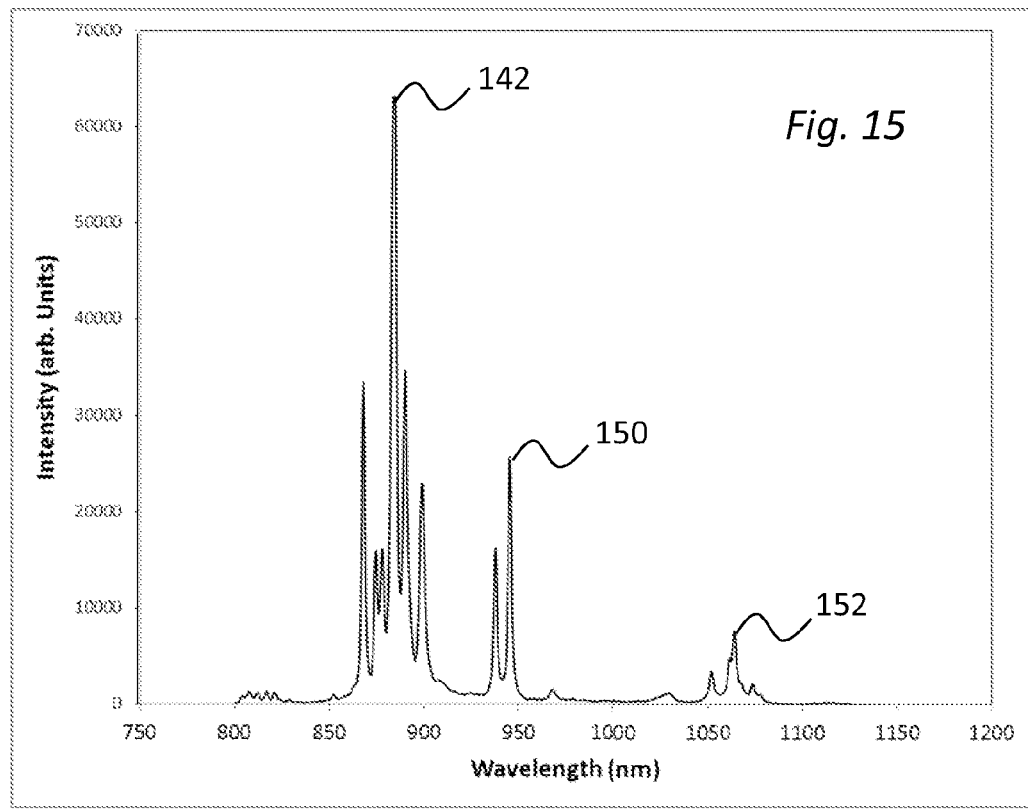
FIG. 15 is a graphic representation of a spectrum having simple or complex information content.
Figure 14:
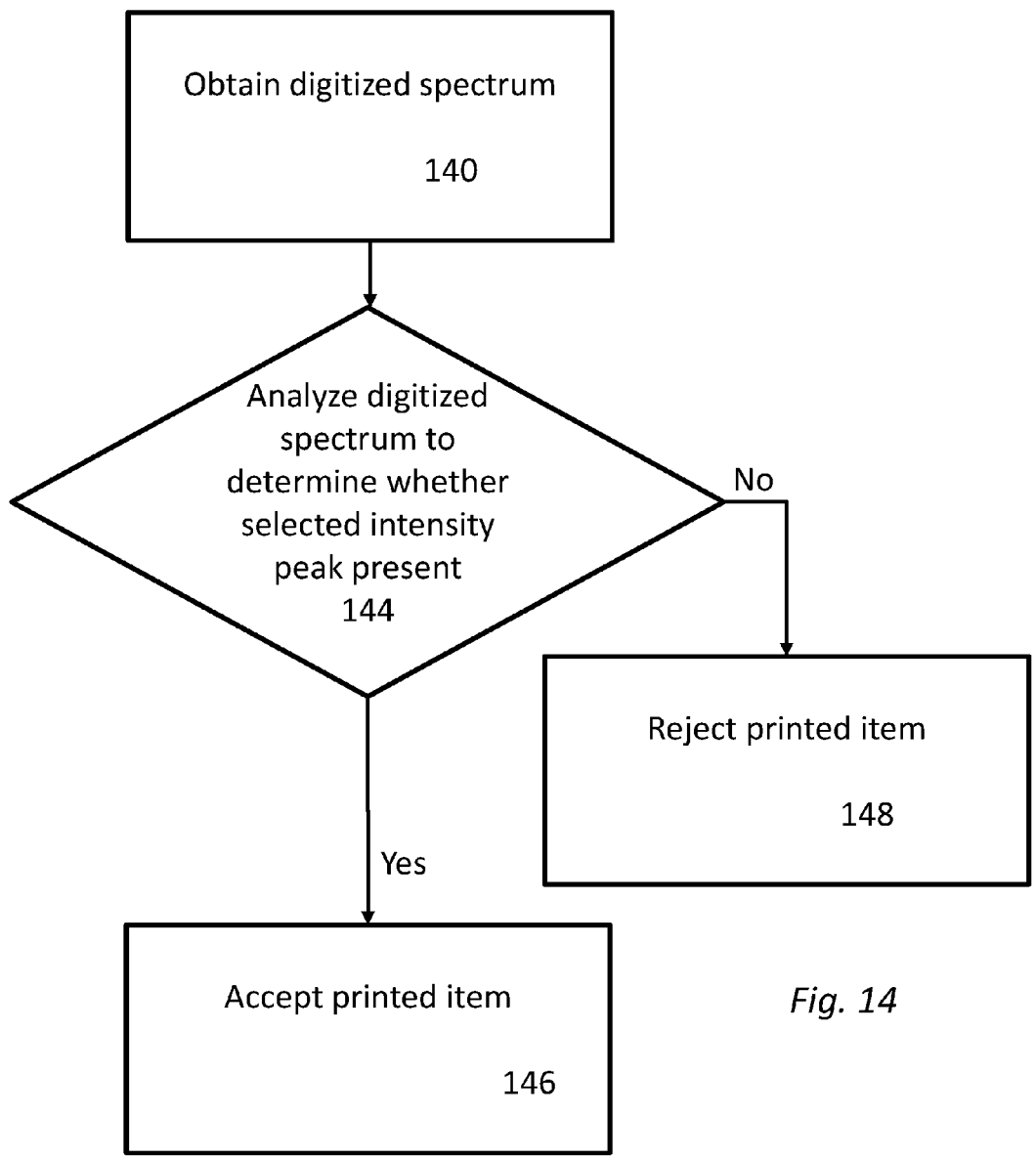
FIG. 14 is a flow chart depiction of a process decision based upon simple information content.

FIG. 14 illustrates the steps included in the execution of a representative processing decision based upon simple information content. In the FIG. 14 example, the decision is a general quality control decision; whether to accept or reject each individual printed item in a production line or analysis line of printed items. As noted above, the inline reader 100 may acquire one or multiple spectra from a target where each spectrum may have multiple spectral features (Step 140). For example, FIG. 15 is a graphic representation of a luminescence spectrum obtained upon excitation of a material with a 785 nm laser source. In this example it may be assumed that the spectrum is obtained from one of the inks used to prepare the printed item. If the ink is absent from a selected printed item, the spectrum will be affected and it may be concluded that the printed item should be rejected.

It may be noted that the spectrum illustrated in FIG. 15 has a single highest intensity peak 142 at about wavelength 880 nm. Analytical software associated with the data processing system 122 could be configured to detect the presence or absence of the intensity peak 142 of the spectrum obtained from each target (each printed item in this example) (Step 144). The presence of the peak correlates with the presence of the desired ink. If the peak 142 is detected, the decision to accept the interrogated printed item may be made automatically (Step 146). Similarly, if the peak is absent, the decision to reject that particular item may be made automatically (Step 148). The forgoing is an example of a decision being made based upon simple information content extracted from a spectrum. In particular, one extracted data point is used to make one processing decision.

Figure 16:
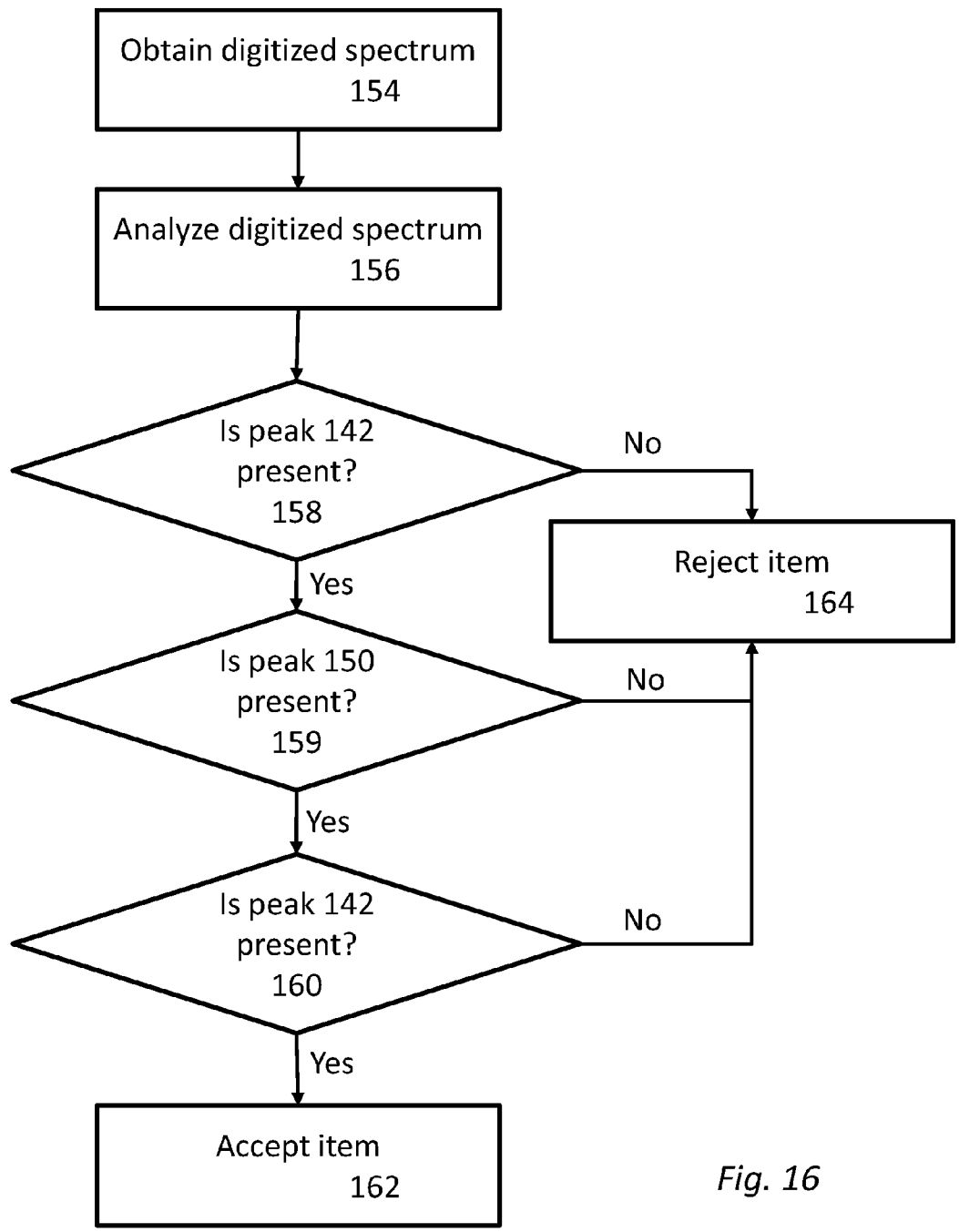
FIG. 16 is a flow chart depiction of a process decision based upon complex information content.

The use of simple information content as the basis for a processing decision can be limiting. For example, in the FIG. 14 process, it is very possible that the correct ink is present in the printed item, but in an incorrect amount. This would result in an unacceptable printed item still being accepted by the inline spectroscopic reader 100 because of the limitations associated with simple information content. A great deal of enhanced flexibility and accuracy can be obtained by basing production or other decisions upon complex information content. For example, it may be noted that the spectrum of FIG. 15 has regional high intensity peaks 150 and 152 at wavelengths of approximately 945 nm and 1070 nm respectively. As illustrated in FIG. 16, the data processing system 122 may be configured to obtain a digitized spectrum from the item (Step 154) and detect each of the regional intensity peaks; 142, 150 and 152 (Steps 156-160). If all three peaks are present the item may be accepted (Step 162). If any one peak is absent the item may be rejected (Step 164). Thus, a single "accept or reject" quality control decision may be based upon complex information content of three independent data points.

It may also be noted from FIG. 15 that the representative spectrum has intensity peaks of a measurable intensity which correlates to (for example) the quantity of ink present at the interrogation spot. A quality control of other processing decision may be made based upon calibrated intensities in conjunction with the presence or absence of selected spectral features. For example, a worn out item might exhibit less intense spectral peaks than a new item because of the wear based erosion of an inherently active spectroscopic material or the wear based reduction in the quantity of a taggant. Complex information content in the form of the relative intensities of multiple intensity peaks may thus be analyzed to sort worn items from new items. It may further be observed that the spectrum of FIG. 15 includes twelve or more spectral intensity peaks. If this spectrum were obtained from a specific spectroscopically active tag, the detection of the presence and/or intensities of multiple peaks can be used to authenticate a tagged item. A non-authentic item might be illegally prepared using an illegitimate taggant that mimics the most intense peak 142. Automatic spectroscopic analysis that is based upon simple information content, for example the detection of a single data point, the presence of intensity peak 142, would incorrectly determine that the non-authentic item was legitimate. An alternative system that bases a decision of authenticity upon complex information content, for example the presence of multiple spectral features, and/or multiple relative spectral intensities or other data is far less likely to incorrectly determine the authenticity of the tagged item.

Another example of a situation where highly automated inline spectroscopic process control based upon complex information content would be valuable is in the quality control of pharmaceutical tablets. It would be useful to interrogate each pill individually to ascertain (a) if an appropriate amount of active pharmaceutical ingredient (API) is present and (b) if there are any spectral impurities present. A typical drug manufacturer will be producing thousands or even millions of pills per day, meaning the time available for each analysis is small. The system must detect the active ingredient and any impurities in a non-destructive fashion, making optical interrogation an analysis method of choice. In particular, many active pharmaceutical ingredients have high-information Raman spectra that are molecule-specific. Different manufacturing lines (whether in a single site or in different companies) will have different drugs, with different Raman spectra. Thus, this manufacturing process application requires a reader capable of acquiring and analyzing one or more unique and complex Raman spectral fingerprints in real time.

In many applications a reader or multiple readers are necessary to detect the presence of a taggant or to detect an intrinsic complex information-rich spectral fingerprint. In one embodiment, Raman or SERS-active particles and materials in the tagged items are detected with a reader capable of measuring inelastically scattered light and contemporaneously determining the identity of the tagged item from the scattered light. As noted above, the reader requires one or more excitation light sources that illuminate the tagged item. The inelastically scattered light from the Raman or SERS-active species is then collected. The spectrum of scattered light is analyzed and the identity of the particles, and hence information about the item is determined. In this embodiment the reader includes a Raman spectrometer.

The light source used to excite the spectroscopically active material or tag may be a monochromatic light from a laser, for example, either a solid state, gas or liquid laser. The laser can be a continuous or pulsed laser. A continuous laser can have powers from 0.1 femtowatt up to 1 megawatt. A pulsed laser can have similar total power ratings with pulses as short as less than 1 femtosecond. The pulse repetition rate can be up to 1 terahertz or as slow as 1 Hz. In addition to lasers, the light can come from an electroluminescent material such as a light emitting diode. The light can come from an incandescent or fluorescent light source. It is also possible to use two (or more) light sources for excitation. In some cases, the light sources can be identical. In others, the light sources operate at different intensities and/or frequencies and/or repetition rates. Alternatively, one light source may be monochromatic, and the other polychromatic. One or more of the light sources could be incandescent.

In selected embodiments one excitation wavelength is in the ultraviolet to NIR range corresponding to light wavelengths from 250 nm to 1600 nm. The laser used may be a laser diode. Specific wavelengths selected for use correspond to specific lasers, including but not limited to 488 nm, 532 nm, 633 nm, 635 nm, 785 nm, 808 nm, 980 nm, 1064 nm, 1310 nm, or 1546 nm. In other embodiments the excitation wavelength range can be from 200 nm to 50 microns. The excitation light can be spectrally or temporally filtered with discrete filters or spatially dispersing elements.

In some embodiments, the monochromatic light spectral width is less than 0.1 nm. In other embodiments, the spectral bandwidth is from 0.0001 nm to 100 nm.

In several embodiments, the excitation and collected light is optically coupled to and from the target under interrogation with lenses, mirrors, light pipes, gratings, waveguides or any other component. These elements can be placed in free space, or all associated with optical fibers. All elements can, but alternatively may not be integrated into a single platform. In one configuration the excitation light source and collection system are connected to the transmission and collection optics with light pipes or optical fibers. In other embodiments, discrete optical elements connect the light source and detection elements. Discrete optics may include but are not limited to lenses, bandpass filters, notch filters, birefringent filters, liquid crystal tunable filters, mirrors or other waveguides.

As noted above, the collected light is analyzed by a spectrometer. The spectrometer typically uses a grating to disperse the collected light onto an area array detector, for example a Charge Coupled Device (CCD). The CCD divides the spectrum into bins. Each bin may correspond to a given wavelength range; the number of bins used can range from 1 bin to many thousands of bins. In one embodiment, the number of bins is more than 20. Linear array detectors, or other types of array detectors can be utilized. In addition to array detectors, other types of detectors can be used such as photomultiplier tubes, photodiodes, and avalanche photodiodes.

One or more optics of the spectrometer may define a specific spectral resolution. In some embodiments, the resolution is less than 10 nm or between 1 nm to 4 nm. In other embodiments, the resolution is from 0.01 nm to 5000 nm. Expressed in wavenumbers, the resolution can be 0.01 $cm^{-1}$ to 40000 $cm^{-1}$.

As described in detail below, the acquired spectrum may be analyzed by a data processing system 122 to determine the presence of a taggant or an intrinsically spectroscopic substance. In addition, the acquired spectrum may be analyzed to determine the presence of a taggant or an intrinsically spectroscopic substance only after accounting for the presence of other materials contributing to the spectrum, i.e. other active or inactive pharmaceuticals, inks, materials, paper, plastic, holograms, threads, fibers, lacquer, or paints. Likewise, the spectrum may also comprise contributions from unwanted additional spectral features, such as background light (e.g. sunlight, fluorescent light), soiling etc. In a third scenario, the acquired spectrum may be analyzed for the taggant or spectroscopically active substance and other spectral contributors (both known and known) simultaneously.

The inline reader embodiments disclosed herein may be incorporated as components of another machine. For example, in embodiments where the reader is proximal to the inline samples there may be allocated a slot (or several slots) in the larger machine for the reader, and in such an instance the reader must both be of particular dimensions as defined by the slot(s) and must also have an appropriate mechanical interface to the larger machine so it can be securely mounted. For example, in one embodiment the entire reader plus all processing electronics, optics, and power supplies may be configured to fit into a space of approximately 65 mm×150 mm×150 mm. The mechanical interface may be "universal", to allow a wide variety of readers with the correct interface to be swapped in and out of a slot at will, or it might be "custom" to allow a single reader to be inserted. In another scenario, it is not necessary for the reader to be proximal to the samples, so long as they are optically coupled (i.e. with an optical fiber). In such an open architecture, size restrictions place upon the reader may be relaxed.

In both open and closed architectures, it is desirable to have a barrier between the optical elements and the samples, for the purpose of keeping the optical element clean. For example, in a pill manufacturing apparatus, a glass window may be placed between a Raman reader and the pill conveyor belt, so that the optical elements are not contaminated with pill dust. This is especially important if more than one type of pharmaceutical tablet is manufactured on the same machine. The barrier material should be chosen to provide a minimal or negligible background signal. For example, if a fluorescent taggant is added to tax stamps, the glass (or other barrier material) should be non-fluorescent.

The larger machine with which an inline reader may be associated can be involved in multiple functions at multiple locations, including but not limited to the following examples. (1) It can be used for process monitoring in the manufacture of materials. (2) It can be used for quality control or quality assurance of materials after manufacture. (3) It can be used where finished goods are packaged. (4) It can be used for sorting incoming materials (e.g. packages at a parcel shipping concern, or pieces of mail at the local, regional, national, or international level). (5) It can be used at dispensing stations (e.g. at a pharmacy or a fuel depot). (6) It can be used at a checkpoint (e.g. automated highway toll station, border crossing, airport check-in/boarding, or cargo loading station). In summary, a larger machine incorporating a disclosed reader can be used wherever rapid, sequential optical analysis and real time decision making concerning a large number of items, is required.

Computer implemented instructions are typically needed to control and operate an inline reader device 100 as disclosed herein. In particular, software is needed to control the spectrometer and illumination hardware for the underlying signal acquisition processes. In addition, software is required to accomplish data analysis, communicate output and to control a process or make a decision based upon the output. In one embodiment these two software functions can be entirely segregated. The software program that accomplishes hardware control and signal acquisition could be a simple and open system that can be distributed to one or multiple entities, and would contain generally-known and basic information for low-level hardware/device communication. This aspect of the software required to operate an inline reader 100 would not necessarily contain information specific to any particular entity for end-use.

The second software function of data analysis and output processing can be implemented in a customized and protected environment such as a security-encrypted portion of computer memory. The data analysis software may be used to determine complex or simple information content as described above and base one or more decisions upon the extracted information content. The data analysis software may contain confidential or proprietary information specific to one entity or end-user. The data analysis software can be modified in terms of content and protection for each user to allow distribution of substantially identical hardware platforms to multiple end-user entities with each having separate and potentially confidential analysis programming.

The protected, confidential or unique data analysis software may contain one or multiple methods of data analysis including but not limited to combinations of known or novel analysis algorithms. These analysis algorithms may include but are not limited to recursive, non-recursive, single-pass, multiple-pass, incremental, dynamic, backtracking, randomized, brute force, linear, non-linear, covariant, modified covariant, least-squares, taxonomic, univariate, multivariate, regressive, extrapolative, interpolative, Bayesian, etc. In one embodiment an analysis algorithm may be used alone. In another embodiment multiple analysis algorithms may be used in combination. In another embodiment, multiple analysis algorithms may be used simultaneously while in another embodiment a specific set of analysis algorithms may be used in a specific order. In yet another embodiment the software may contain multiple analysis algorithms where the number, types, and orders utilized may be dependent on the output from one or multiple analyses.

Figure 17:
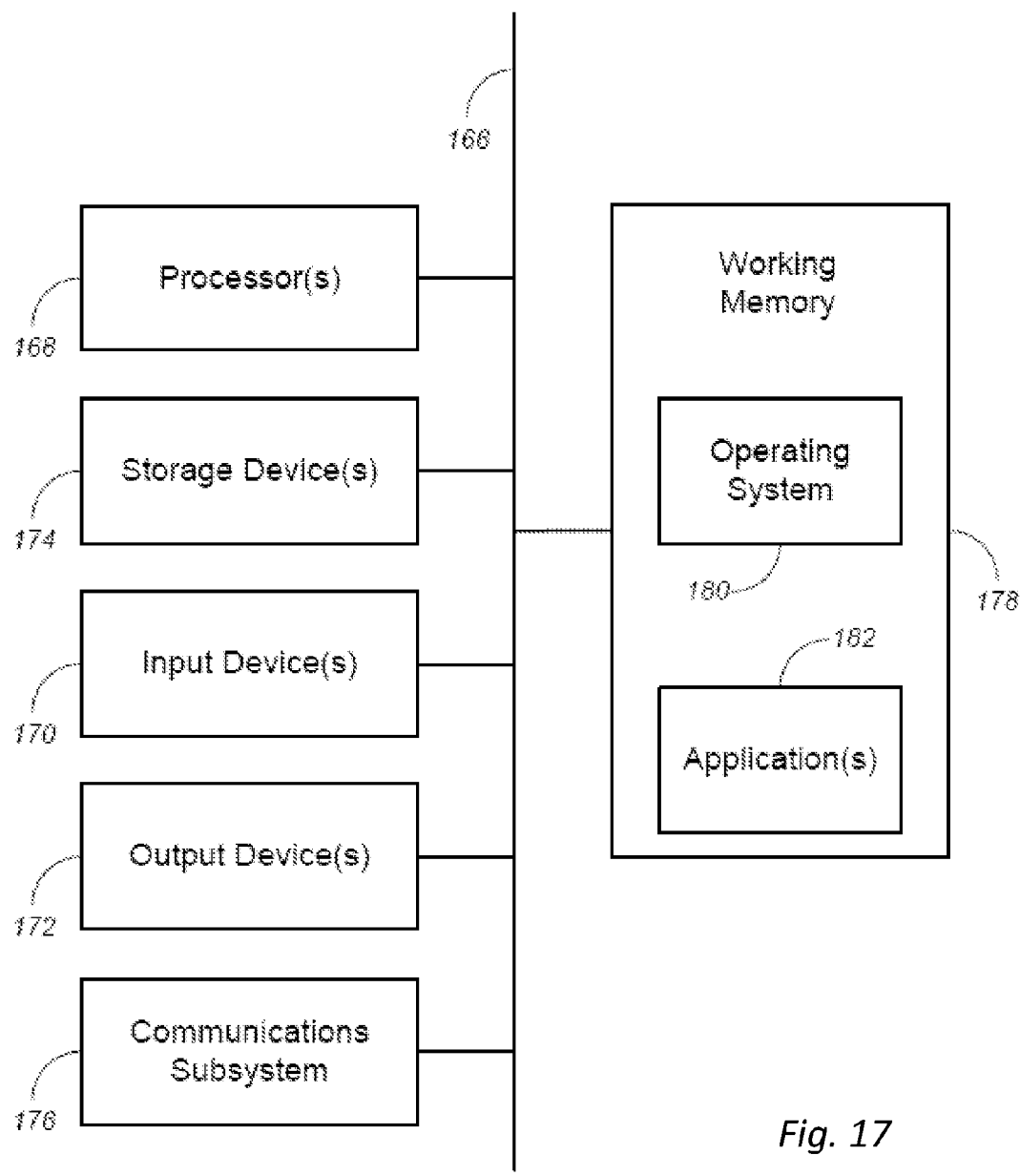
FIG. 17 is a schematic diagram of a data processing system as disclosed herein.

As shown in FIGS. 1, 3, 5, 7 and 9 an unprocessed digital output signal 165 may be read from the detector 120 and provided to a data processing system 122. The signal 165 may be conveyed from the detector 120 electronically in a suitable data cable or wirelessly. Alternatively, the signal 165 may be conveyed by digital optic means in a suitable fiber optic cable. FIG. 17 provides a schematic illustration of one embodiment of a data processing system 122 configured to perform the methods provided by various embodiments, as described herein. It should be noted that FIG. 17 is meant only to provide a generalized illustration of various components, of which one or more (or none) of each may be utilized as appropriate. FIG. 17 therefore, broadly illustrates how individual data processing system elements may be implemented in a relatively separated or relatively more integrated manner.

The data processing system 122 is shown comprising hardware elements that can be electrically coupled via a bus 166 (or may otherwise be in communication, as appropriate). The hardware elements may include one or more processors 168, including without limitation one or more general-purpose processors and/or one or more special-purpose processors (such as digital signal processing chips, graphics acceleration processors, and/or the like); one or more supplemental input devices 170, which can include without limitation a mouse, a keyboard and/or the like; and one or more output devices 172, which can include without limitation a display device, a printer and/or the like.

The data processing system 122 may further include (and/or be in communication with) one or more storage devices 174, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The data processing system 122 might also include a communications subsystem 146, which can include without limitation a modem, a network card (wireless or wired), an infrared communication device, a wireless communication device and/or chipset (such as a Bluetooth™ device, an 802.11 device, a WiFi device, a WiMax device, a WWAN device, cellular communication facilities, etc.), and/or the like. The communications subsystem 176 may permit data to be exchanged with a network (such as the network described below, to name one example), with other computer systems, and/or with any other devices described herein. In many embodiments, the data processing system 122 will further comprise a working memory 178, which can include a RAM or ROM device, as described above.

The data processing system 122 also may comprise software elements as described above, shown as being currently located within the working memory 178, including an operating system 180, device drivers, executable libraries, and/or other code, such as one or more application programs 182, which may comprise computer programs provided by various embodiments, and/or may be designed to implement methods, and/or configure systems, provided by other embodiments, as described herein. Merely by way of example, one or more procedures described with respect to the method(s) discussed herein might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 174 described above. In some cases, the storage medium might be incorporated within a computer system, such as the data processing system 122. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the data processing system 122 and/or might take the form of source and/or installable code, which, upon compilation and/or installation on the data processing system 122 (e.g., using any of a variety of generally available compilers, installation programs, compression/decompression utilities, etc.) then takes the form of executable code.

The terms "machine readable medium" and "computer readable medium," as used herein, refer to any medium that participates in providing data that causes a machine to operation in a specific fashion. In an embodiment implemented using the data processing system 122, various computer readable media might be involved in providing instructions/code to processor(s) 168 for execution and/or might be used to store and/or carry such instructions/code (e.g., as signals). In many implementations, a computer readable medium is a non-transitory, physical and/or tangible storage medium. Such a medium may take many forms, including but not limited to, non-volatile media, volatile media, and transmission media. Non-volatile media includes, for example, optical and/or magnetic disks, such as the storage device(s) 174. Volatile media includes, without limitation, dynamic memory, such as the working memory 178. Transmission media includes, without limitation, coaxial cables, copper wire and fiber optics, including the wires that comprise the bus 166, as well as the various components of the communication subsystem 176 (and/or the media by which the communications subsystem 176 provides communication with other devices). Hence, transmission media can also take the form of waves (including without limitation radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

As noted above, the various inline reader embodiments disclosed herein can be used to read and extract information content from the spectra of two general classes of targets: inherently spectroscopically active targets or alternatively substances, materials or items which have been marked or tagged with a spectroscopically active marker or tag. Many alternative types of marker or tag are discussed below.

In general, taggants are materials, substances, molecules, ions, polymers, nanoparticles, microparticles, or other matter, incorporated into, onto or otherwise associated with objects for the purposes of identification or quantitation. More specifically, taggants are used in activities and products including but not limited to detection, analysis, and/or quantification measurements related to brand security, brand protection, trademark protection, product security, product identification, brand diversion, barcoding, grey market remediation, friend-or-foe analysis, product life cycle analysis, counterfeiting, anti-counterfeiting, forensic analysis of authenticity, authentication, biometrics, object tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, and standoff detection/identification.

Multiple classes of molecules and materials have been used for optical taggants. These include but are not limited to fluorophores, luminophores, phosphors, light scatterers, Raman-active species (including surface enhanced Raman scattering (SERS)-active materials), infrared-active species. In some cases, the photons being detected are of lower energy than the input photons (Stokes-shifted); in other cases, the photons being detected are of high energy than the input photons (anti-Stokes shifted). One could imagine scenarios where both Stokes and anti-Stokes materials are collected and used.

Taggants can be added to all forms of matter, including but not limited to solids, liquids, gases, gels, foams, semi-solids, glasses, plasmas, liquid crystals, amorphous and magnetically-ordered solids, superconductors, superfluids, Bose-Einstein condensates, and supersolids.

Many known methods of detecting taggants utilize one of several spectroscopic techniques, for example a surface-enhanced spectroscopy (SES) techniques such as SERS or SERRS. Broadly speaking, suitable taggant materials fall in two categories: nano-/microscale and macroscopic. For example, certain sizes and shapes of Ag and Au nanoparticles, and aggregates thereof, are known to support SERS. Likewise, a large variety of macroscopic SERS substrates have been described in the literature, including electrodes, evaporated films, Langmuir-Blodgett films, 2-dimensional planar arrays, and so forth.

Known tagging methods which utilize SERS-active tags typically include a reporter molecule or dye with known SERS-active characteristics. For example, a known SERS-active chemical can be added as a dye to mark fuel and a subsequent SERS spectrum obtained when the SERS-active dye is associated with a SERS-active metal particle or substrate.

The inline reader embodiments disclosed herein can be configured to extract information content from a surface-enhanced spectroscopy (SES) active taggant. The most widely studied have been surface-enhanced Raman scattering and surface-enhanced fluorescence (SEF). However, a variety of other surface enhanced phenomena have been observed including surface-enhanced hyper Raman scattering (SE-HRS), surface-enhanced hyper Raman resonance scattering (SEHRRS), surface-enhanced Rayleigh scattering, surface-enhanced second harmonic generation (SHG), surface-enhanced infrared absorption reflectance (SEIRA), and surface-enhanced laser desorption ionization (SELDI). These are part of a wider field known as plasmon enhancement or plasmon-enhanced spectroscopy, which in addition to the phenomena mentioned above includes surface plasmon enhanced emission (such as SPASERS—surface plasmon amplification of spontaneous emission of radiation), plasmon enhanced diffraction, and plasmon enhanced optical transmission. Plasmon enhancement is also a method to increase the efficiency of solar cells. As used throughout this disclosure SES includes the above listed and any related or similar spectroscopic technique.

One type of known SERS-active nanoparticle is a SERS nanotag, as described in U.S. Pat. No. 6,514,767, U.S. Pat. No. 6,861,263, U.S. Pat. No. 7,443,489 and elsewhere. All matters disclosed in U.S. Pat. No. 6,514,767, U.S. Pat. No. 6,861,263 and U.S. Pat. No. 7,443,489 are incorporated herein in their entirety for all matters disclosed therein. In a conventional SERS nanotag composition, a reporter molecule is adsorbed to a SERS-active surface, and both the SERS-active surface and the reporter are encapsulated, typically with silica or a glass. One advantage of a silica coating is that it prevents the adsorbed molecule from diffusing away, and also prevents other molecules from adsorbing to the surface. This imparts a level of robustness and environmental insensitivity to the SERS nanotag particles that is, for many applications, a desirable feature.

Surface enhanced Raman scattering (SERS)-active particles are useful in a variety of applications. One interesting application is anti-counterfeiting, and more specifically to verify the authenticity, source, age, and/or distribution path of banknotes, tax stamps, banderols, passports, identification cards, driver's licenses, work permits, fiduciary documents, stock and bond certificates, and other valuable documents that contain ink. Likewise, SERS-active particles can be used for similar purposes to mark or tag a variety of other materials that contain print or lettering composed of ink or lacquer, including but not limited to software, machine parts such as airplane parts or automobile parts, instrumentation, pharmaceutical and diagnostic products, medical devices, luxury goods, fast-moving consumer goods, CD's, DVD's and other electronic storage components, and so forth. Moreover, any ink- or lacquer-containing packaging for any type of product is a viable location for introduction of SERS-active particles for anti-counterfeiting, or authentication purposes. Additional closely related applications for SERS-active particles include: brand security, brand protection, trademark protection, product security, product identification, brand diversion, barcoding, grey market remediation, friend-or-foe analysis, product life cycle analysis, counterfeiting, forensic analysis of authenticity, biometrics, document tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, object tracking, standoff detection, and/or standoff identification. In addition, SERS-active particles can be used for combinations of these applications, including but not limited to a combination of authentication and sell-by-date tracking. Collectively, these applications are referred to as Industrial Security.

Examples of specific materials or objects that can be tagged with the particles disclosed herein, or into which the particles can be incorporated include, but are not limited to:
Packaging, including adhesives, paper, plastics, labels, and seals
Agrochemicals, seeds, and crops
Artwork
Computer chips
Cosmetics and perfumes
Compact disks (CDs), digital video disks (DVDs), and videotapes
Documents, money, and other paper products (e.g., labels, passports, stock certificates)
Inks, paints, varnishes, lacquers, overcoats, topcoats, and dyes
Electronic devices
Explosives and weapons
Food and beverages, tobacco
Textiles, clothing, footwear, designer products, and apparel labels
Polymers
Insects, birds, reptiles, and mammals
Powders
Luxury goods
Other anti-counterfeiting substances or materials, such as holograms, optically variable devices, color-shifting inks, threads, and optically-active particles
Hazardous waste
Movie props and memorabilia, sports memorabilia and apparel
Manufacturing parts, automobile parts, aircraft parts, truck parts
Petroleum, fuel, lubricants, gasoline, crude oil, diesel fuel, fuel additive packages, crude oil
Pharmaceuticals, prescription drugs, over-the-counter medicines, and vaccines

EXAMPLES

Example 1

Inline Detection of an Intrinsic Signal

Figure 18:
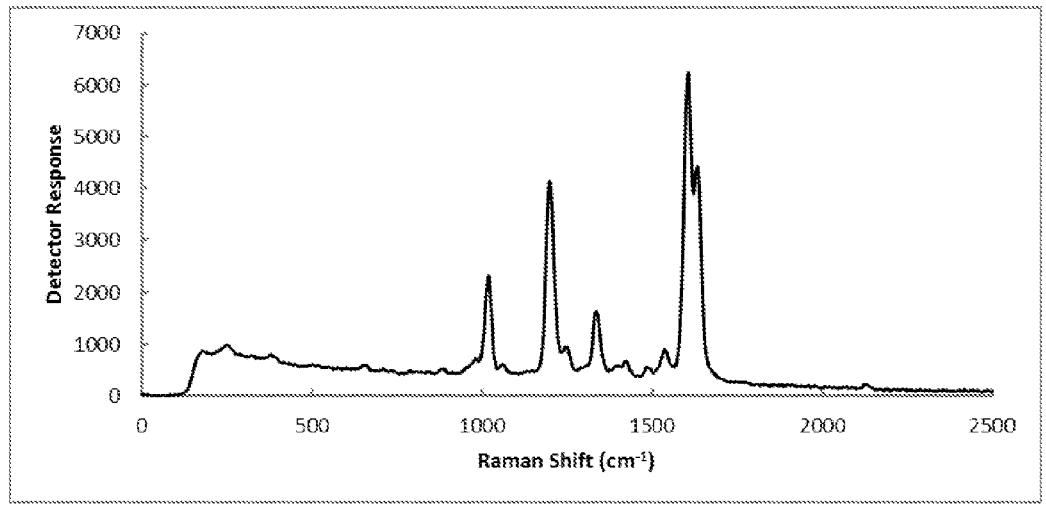
FIG. 18 a graphic representation of a spectrum obtained by inline, high-speed detection of organic crystals.

Example 1 illustrates the inline, high speed, detection of an intrinsic spectroscopic signal. Thus, Example 1 shows the feasibility of the process monitoring of discrete intrinsically spectroscopic items such as pharmaceutical tablets having unknown exact positions on a moving belt. Approximately 100 mg of 1,2-bis-(4-pyridyl) ethylene (BPE) crystals were placed in a 1 $cm^2$ area on a 65 mm×155 mm piece of cotton paper and affixed with a strip of optically-transparent adhesive tape. The paper was loaded onto the outside of a 0.75 m diameter cylindrical drum and the drum was driven at 10 m/s tangential velocity. At this rate, a simulated pill that is 1 cm in diameter moves past the optical head in 1 ms. The moving sample on the outside of the drum was irradiated with approximately 180 mW of 785 nm laser light for a total integration time of 6 ms to ensure complete capture of the event. The beam size was 150 microns in diameter. The total irradiated area was 150 microns×6 cm (6 ms×10 m/s), and of this area, the portion that contained the BPE crystals was 150 microns×1 cm (⅙ the total area being interrogated—selected to match reasonable pill dimensions). The intrinsic Raman spectrum of BPE was acquired is shown in FIG. 18.

Example 2

Inline Detection of a Taggant in Ink

Figure 19:
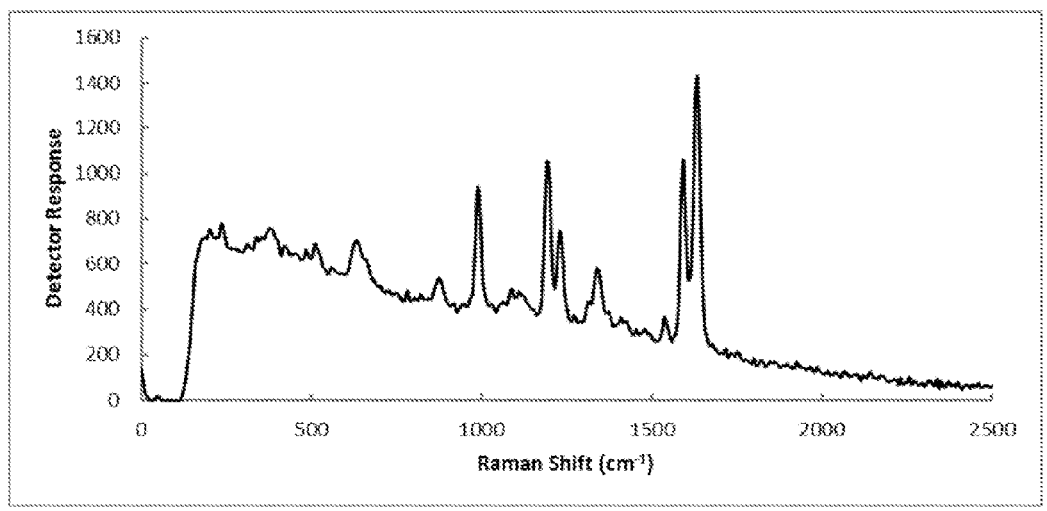
FIG. 19 a graphic representation of a spectrum obtained by inline, high-speed detection of spectroscopically active taggants in ink.

Example 2 illustrates the inline, high speed detection of a spectroscopically active taggant affixed to an item. Thus, Example 2 shows the feasibility of spectroscopic process monitoring of discrete tagged items such as the detection of a tagged printed sample on a moving belt. SERS nanotags (as described above) were added to an orange offset ink. The tags comprised 90-nm Au core particles, 1,2-bis-(4-pyridyl) ethylene (BPE) reporter molecules and an approximately 50-nm thick silica shell. The taggant loading rate was 0.1% w/w (Au basis). The ink sample was applied at a thickness of <10 microns over a 1 $cm^2$ area onto a sheet of 65 mm×155 mm cotton paper, and was loaded onto the outside of a 0.75 m diameter cylindrical drum that was driven at 10 m/s tangential velocity. The moving sample on the outside of the drum was irradiated with approximately 180 mW of 785 nm laser light for a total integration time of 5 ms. The beam size was 150 microns in diameter. The total irradiated area was 150 microns×5 cm (5 ms×10 m/s), and of this area, the portion that contained the SERS nanotags was 150 microns×1 cm (⅕ the total area being interrogated). The acquired Raman spectrum of the BPE-loaded SERS tags in orange ink is shown in FIG. 19.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. An inline spectroscopic reader comprising:
   a light source;
   a conveyor belt;
   two or more optics heads comprising transmission optics providing for the illumination of a target at two or more spatially distinct locations with light from the light source, wherein the target is moving on the conveyor belt with respect to the transmission optics, and detection optics providing for the simultaneous collection of light from each of the two or more spatially distinct locations on the target;
   a spectrometer in optical communication with the two or more optics heads, the spectrometer having a single detector providing for two or more digital spectrum outputs from different regions of the detector with each spectrum output corresponding to one of the two or more spatially distinct locations on the target; and
   a data processing system in digital communication with the detector providing substantially contemporaneous spectroscopic analysis of the light collected from the target including discrete digital spectrum outputs from light collected from each of the two or more spatially distinct locations on the target wherein the data processing system is configured to extract information content from at least one of the digital spectrum outputs and identify two or more Raman spectroscopic peaks in the digital spectrum output implementing the two or more Raman spectroscopic peaks identified to support a single process decision.

2. The inline spectroscopic reader of claim 1 further comprising fiber optic coupling between the light source, the multiple optics heads and the spectrometer.

3. The inline spectroscopic reader of claim 1 wherein illumination of the target is provided along a linear illumination zone.

4. The inline spectroscopic reader of claim 1 wherein the light source is a laser providing light emission having at least one discrete wavelength.

5. The line spectroscopic reader of claim 1 wherein the data processing system provides for the autonomous implementation of a processing decision based upon the identification of two or more spectroscopic peaks from the digital spectrum output.

6. The inline spectroscopic reader of claim 5 wherein the information content extracted from the digital spectrum output comprises the determination of the presence of multiple spectral intensity peaks or the determination of multiple relative spectral intensities.

7. The inline spectroscopic reader of claim 6 wherein the information content extracted from the digital spectrum output comprises the determination of the presence of multiple spectral intensity peaks and the determination of multiple relative spectral intensities.

8. The inline spectroscopic reader of claim 1 further comprising a non-transitory digital storage medium having instructions encoded thereon providing for spectroscopic signal acquisition and a separate digital storage medium having instructions encoded thereon providing for spectroscopic data analysis.

9. The inline spectroscopic reader of claim 1 further comprising an integrated non-transitory digital storage medium having instructions encoded thereon providing for spectroscopic signal acquisition and having instructions encoded thereon providing for spectroscopic data analysis.

10. The inline spectroscopic reader of claim 1 wherein the spectroscopic analysis comprises the detection of a Raman spectrum.

11. The inline spectroscopic reader of claim 10 wherein the spectroscopic analysis comprises the detection of a surface enhanced Raman spectrum.

12. A method of inline spectroscopy comprising:
   conveying a target on a conveyor belt past two or more optics heads;
   illuminating the target at two or more spatially distinct locations with light from a light source transmitted through transmission optics associated with each of the two or more optics heads;
   simultaneously collecting light from the target at the two or more spatially distinct locations through collection optics associated with each of the two or more optics heads wherein the target is moving with respect to the spectrometer when light is collected from the target;
   obtaining two or more digitized spectra with a spectrometer from the collected light, wherein the digitized spectra are obtained from a single spectroscopic detector providing for two or more digital spectrum outputs from different regions of the single detector with each spectrum output corresponding to one of the two or more spatially distinct locations on the target;
   extracting information content from at least one of the digitized spectra; and
   basing a contemporaneous process decision upon the information content extracted from the digitized spectrum, identifying two or more Raman spectroscopic peaks from the digitized spectrum, and basing the process decision upon the identification of the presence of two or more Raman spectroscopic peaks in the digitized spectrum.

13. The method of inline spectroscopy of claim 12 further comprising obtaining a digitized Raman spectrum from the collected light.

14. The method of inline spectroscopy of claim 12 further comprising obtaining a digitized surface enhanced Raman spectrum from the collected light.

* * * * *